(12) United States Patent
Miguez et al.

(10) Patent No.: US 7,670,824 B2
(45) Date of Patent: Mar. 2, 2010

(54) **MULTICOPY-INTEGRATION OF HETEROLOGOUS GENES AND EXPRESSION IN *METHYLOBACTERIUM***

(75) Inventors: Carlos B. Miguez, Beaconsfield (CA); Young-Jun Choi, Pierrefonds (CA)

(73) Assignee: National Research Council of Canada, Ottawa (CA)

( * ) Notice: Subject to any disclaimer, the term of this patent is extended or adjusted under 35 U.S.C. 154(b) by 348 days.

(21) Appl. No.: 11/492,822

(22) Filed: Jul. 26, 2006

(65) Prior Publication Data
US 2008/0026005 A1 Jan. 31, 2008

Related U.S. Application Data

(60) Provisional application No. 60/702,291, filed on Jul. 26, 2005.

(51) Int. Cl.
*C12N 1/20* (2006.01)
*C12N 15/00* (2006.01)
*C12N 15/74* (2006.01)

(52) U.S. Cl. ............... 435/252.3; 435/69.1; 435/320.1; 435/471; 536/24.1

(58) Field of Classification Search ............... 435/69.1, 435/252.3, 320.1, 471; 536/24.1
See application file for complete search history.

(56) References Cited

OTHER PUBLICATIONS

Choi, K.-H., et al. A Tn7-based broad-range bacterial cloning and expression system. Nature Methods, vol. 2, No. 6, pp. 443-448, Jun. 2005.*
Gutierrez, J., et al. FEMS Microbiology Letters, vol. 248, No. 1, pp. 125-131, Jul. 1, 2005.*

* cited by examiner

*Primary Examiner*—Rodney P. Swartz
(74) *Attorney, Agent, or Firm*—Johanna Coutts

(57) ABSTRACT

The integration of genes into methylobacterium, such as *M. extorquens* ATCC is disclosed, using a transposon system, preferably the mini-Tn7 transposon system, and under the control of a promoter, such as the strong methanol dehydrogenase promoter ($P_{mxaF}$). Multicopy integration of genes of interest is also disclosed. The unique and specific attachment site for the Tn7 attachment (attTn7) is identified for *M. extorquens*.

21 Claims, 7 Drawing Sheets

US 7,670,824 B2

MULTICOPY-INTEGRATION OF HETEROLOGOUS GENES AND EXPRESSION IN *METHYLOBACTERIUM*

RELATED APPLICATIONS

This Application claims priority to U.S. Provisional Patent Application No. 60/702,291, filed Jul. 26, 2005.

FIELD OF THE INVENTION

The invention relates to the transformation of host prokaryotic cells with one or more copies of genes, such that the genes are expressed in the host cells.

BACKGROUND OF THE INVENTION

*Methylobacterium extorquens* is a pink-pigmented facultative methylotroph (PPFM) capable of growth on simple and inexpensive single-carbon compounds, such as methanol, as the sole carbon and energy source in a completely synthetic mineral salt medium (Bourque et al., 1992). These simple requirements combined with the fully automated nutrient non-limiting high cell density fed-batch bioprocesses developed for *M. extorquens* ATCC 55366 (Bourque et al, 1995; Bélanger et al., 2004; Beland et al., 2004), render large-scale *M. extorquens* fermentations very cost-effective. This feature, along with the availability of genetic tools (Marx and Lidstrom, 2001; Figueira et al., 2003; Choi et al., 2004) and abundant genome sequence information and stoichiometric models for evaluating its metabolic capabilities (Van Dien and Lidstrom, 2002), makes *M. extorquens* very interesting economically as a host for the production of recombinant proteins. Overexpression in *M. extorquens* of recombinant green fluorescent protein, esterase from *Lactobacillus casei*, catechol 2,3-dioxygenase from *Pseudomonas putida*, enterocin P from *Enterococcus faecium*, and haloalkane dehalogenase from *Xanthobacter autotrophicus* have been described in the literature (Fitzgerald and Lidstrom, 2003; Bélanger et al., 2004; Choi et al., 2004; Gutierrez et al., 2005).

*Methylobacterium* strains are ubiquitous in nature, inhabiting soils (Sy et al., 2001), sediments and fresh water environments (Rickard et al., 2002). *Methylobacterium* strains have also been detected and isolated from the surface of leaves from almost all plants tested (Romanovskaya 2001; Omer et al., 2004; Koopman and Kutschera, 2005; Gallego et al., 2005). Furthermore, there are a growing number of reports describing favourable interactions between PPFMs and plants. *M. extorquens* has been described as an endophytic microorganism, found in the stem and leaves of citrus plants (Lacava et al., 2004), as a bud endophyte of Scots pine (Pirttila, 2000), and in the rhizosphere of flowering plants (Idris et al., 2004).

Recently, our laboratory has successfully cloned and expressed in *M. extorquens* the cry1Aa gene. The toxin protein encoded by cry1Aa is highly active against the spruce budworm, a powerful forest defoliating pest. These observations in view of the ubiquitous nature of *M. extorquens* in the environment and the ease by which the strain can be genetically transformed to over-express recombinant proteins, suggests that this microorganism could be utilized as an attractive delivery system of recombinant biocontrol agents against crop and forest insect pests. However, the utilization of expression systems in the environment or under high cell density fermentation bioprocesses can be problematic. The reason for this being plasmid segrational instability in the absence of selective pressure. The loss of plasmid and consequently the loss of expression of the desired recombinant product occurs gradually but surely under growth conditions where antibiotics cannot be used for practical or safety issues. We have shown in a previous study (Bélanger et al., 2004) that approximately 50% of recombinant expression is lost following 15 generations of growth in the absence of selective pressure in *M. extorquens*. Integration of expression cassettes in bacterial chromosomes would not necessitate the use of antibiotic selection for the stable expression of recombinant products. It has been recently shown that the Tn7 system integrates, in a stable and site-specific manner, recombinant DNA fragments into a site of the chromosome called attTn7. This attTn7 is located in the intergenic region downstream of the glmS gene in many Gram negative bacteria such as *E. coli, Klebsiella pneumonia, Serratia marcescens, Pseudomonas putida* and *Yersinia pestis* (Craig, 1989; Lichtenstein and Brenner, 1982; Choi et al., 2005).

SUMMARY OF THE INVENTION

A first object of the invention is to provide *Methylobacterium* cells, and preferably *M. extorquens* cells, capable of expressing genes of interest, preferably without need for antibiotic selective pressures, and preferably without inactivation of host cell genes. This is preferably achieved using the mini-Tn7 transposon system, at least one gene of interest, and a suitable promoter.

A further object of the invention is to provide *Methylobacterium* cells, and preferably *M. extorquens* cells, capable of expressing multiple copies of genes of interest.

A further object of the invention is to identify the mini Tn7 transposon system integration site of *M. extorquens.*

A first aspect of the invention provides for a vector for the integration of at least one gene into the genetic material of a *Methylobacterium* host cell such that the gene may be expressed by the host cell, the vector comprising a promoter operably linked to said at least one gene, and a transposon system.

A second aspect of the invention provides for a *Methylobacterium* host cell that has been transformed with a vector comprising at least one gene of interest, a promoter operably linked to said at least one gene, and a transposon system.

A further aspect of the invention provides for a method for producing a polypeptide encoded by at least one gene, comprising the step of culturing *Methylobacterium* host cells that have been transformed with a vector comprising at least one gene of interest, a promoter operably linked to said at least one gene, and a transposon system.

A further aspect of the invention provides for the use of a *Methylobacterium* host cell that has been transformed with a vector comprising at least one gene of interest, a promoter operably linked to said at least one gene, and a transposon system, as a biopesticide or for tracking the movement and growth of the host cell.

BRIEF DESCRIPTION OF THE DRAWINGS

FIG. 1 is a schematic drawing illustrating construction of mini-Tn delivery plasmids.

FIG. 2 is a series of southern hybridization blot profiles of BGL, EST and GFP, wherein M; marker, bgl; B-galactosidase, estI; esterase, gfp; green fluourescent protein, and wherein chromosomal DNA was isolated from each recombinant, and digested with salI, then hybridized.

FIG. 3 is a schematic illustration showing the mini-Tn7 integration site (attTn7) in *M. extorquens* (SEQ ID NO: 1).

FIG. 4 is a schematic illustration showing the PCR identification of mini-Tn7 integration in *M. extorquens*. Verification of transposition events by colony PCR using the primer pairs shown by convergent arrows yields PCR fragments whose sizes are indicated in bp. Lane 1; wild type, lane 2 and 5; gfp integrants, lane 3 and 6; est integrants, lane 4 and 7; bgl integrants, M; marker.

DETAILED DESCRIPTION OF THE INVENTION

Figure 1:
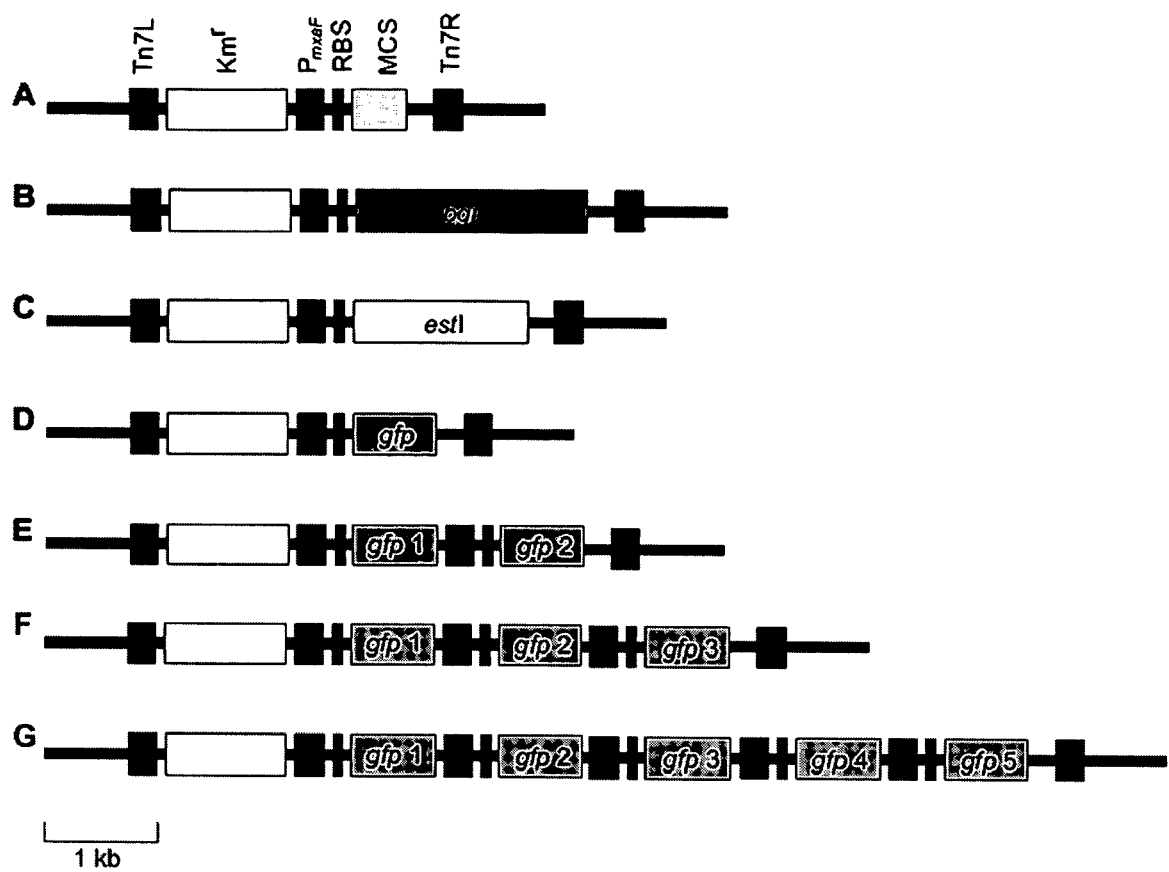

The invention provides transposon-based single and multicopy expression of recombinant genes in *Methylobacterium* cells, including *M. extorquens* ATCC 55366. Using a suitable promoter such as a lac promoter, a T5 promoter, a λ promoter, or a methanol dehydrogenase promoter ($P_{mxaF}$) (preferably a methanol dehydrogenase promoter) and a suitable transposon system such as mini-Tn7, high level expression of chromosomally integrated genes in *Methylobacterium* such as *M. extorquens* ATCC 55366 may be obtained. The methodology also permits multicopy integration of genes of interest. Multicopy transformants (1-5 copies) were obtained with significantly increased GFP yield in correlation with the corresponding copy numbers.

Further, the unique and specific attachment site for the Tn7 attachment (attTn7) was identified for *M. extorquens*. Insertion of heterologous genes in this location did not cause any insertional inactivation of host genes.

More specifically according to the invention, we have established procedures for the construction of genetically engineered, *Methylobacterium* including *M. extorquens*, harbouring chromosomally integrated expression constructs of heterologous DNA sequences encoding such proteins as β-galactosidase, esterase and green fluorescent using the mini-Tn7 integration system. The recombinant *M. extorquens* described herein, contains the methanol dehydrogenase promoter ($P_{mxaF}$) which drives the efficient production of heterologous proteins in the absence of selective pressure for the maintenance of target genes. However, other promoters such as lac promoter, a T5 promoter, a λ promoter have been tested with this system and found to be effective. Further, it is expected that other *Methylobacterium* strains, including methanotrophic strains, having genetic properties highly similar to those of *M. extorquens*, could be similarly transformed with a gene of interest and the mini-Tn7 transposon system. All of the integrated genes tested, bgl, estI and gfp were very stably maintained during fermentation processes in a simple chemically defined mineral salts medium, known as CHOI medium. The stable inheritance of the heterologous genes in *M. extorquens* without selective pressure is of particular interest for "green" bioprocesses, where the use of antibiotics is not desirable. Furthermore, this integration system allows for multi-copy integration of genes of interest in *M. extorquens* resulting in the over-production of recombinant proteins.

Unlike the Tn5-based integration system which randomly integrates DNA fragments into the chromosome potentially causing insertional inactivation of host genes, the Tn7-based system results in stable expression of integrated gene(s). The Tn7 inserts at a specific intergenic site called attTn7, a non-coding region of *M. extorquens* chromosome.

The highest level of GFP expression produced by the five copies of GFP integrated transformants (GFP5) was approximately 20-fold greater than that produced by the single copy integration transformant (GFP1), and about 50% of that produced by transformants harboring the expression cassette on a multicopy plasmid (10 to 30 copies of plasmid per cell). This invention also renders the stable over production of recombinant proteins in *M. extorquens* in the absence of antibiotics possible. Furthermore, using the novel integration system, it is contemplated to simultaneously integrate and express different genes of interest in *M. extorquens*. The present invention also demonstrates that the mini-Tn7 mediated integration system is a valuable tool for the overproduction of multiple enzymes in *M. extorquens* and other methylobacterium, and possesses interesting environmental and commercial applications. For example, a gene encoding a labeling protein could be integrated into host methylobacterium cells in order to track the labeled host cells in plant or soil samples. Further, a gene encoding a toxic protein may be integrated into host methylobacterium cells so that the host cells may be applied to plants as a biopesticide.

Construction of an integrative expression vector for *M. extorquens*. A strong homologous promoter ($P_{mxaF}$), which was derived from the mxaF operon of *M. extorquens* (Marx and Lidstrom, 2001) was applied in the construction of the integrative expression vector. In previous studies, we have used this promoter combined with the T7 RBS to express heterologous proteins in *M. extorquens* (Choi et al., 2004). The promoter and RBS cassette was cloned into a mini-Tn7 transposon system to construct the expression plasmid, pBR170 (FIG. 1A). Chromosomal integration of the mini-Tn7-$P_{mxaF}$-RBS-genes of interest derived from pBR170 was achieved in *M. extorquens* by co-electroporation with a helper plasmid pUX-BF13 providing the Tn7 transposition function in trans (Bao et al., 1991).

Identification of Tn7 Integration Site in *M. extorquens*.

Figure 2:
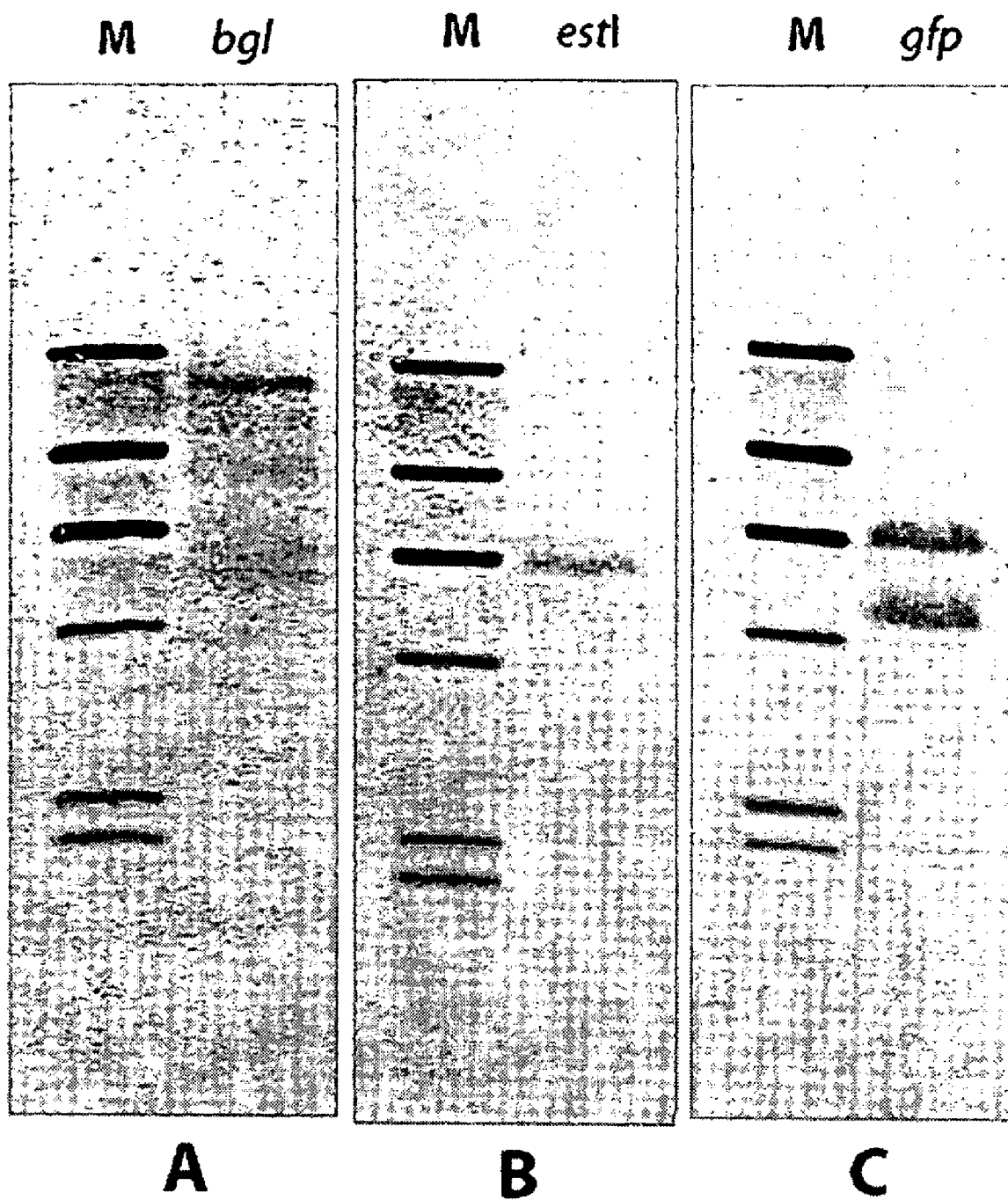
Figure 3:
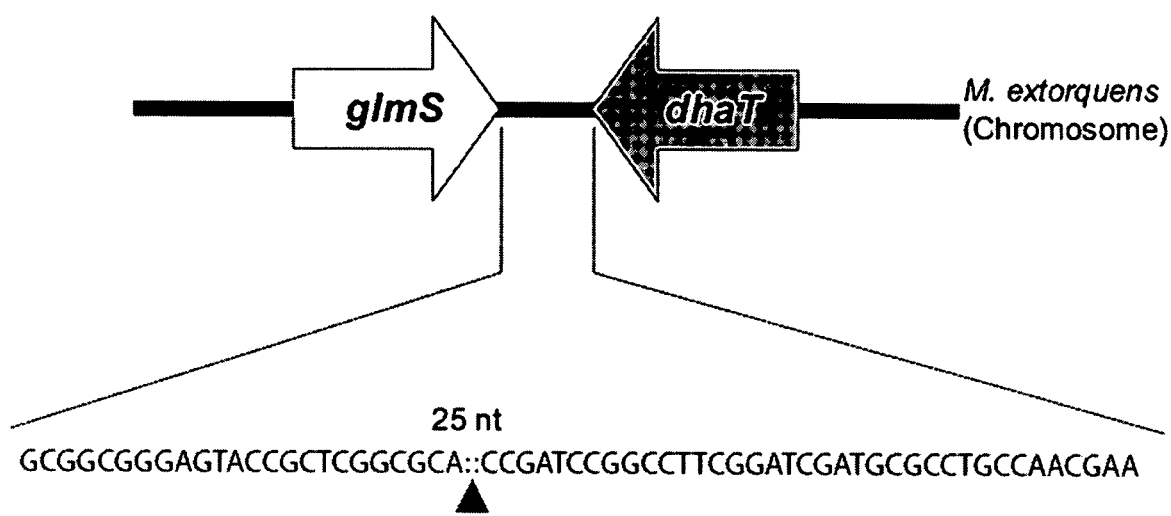
Figure 4:
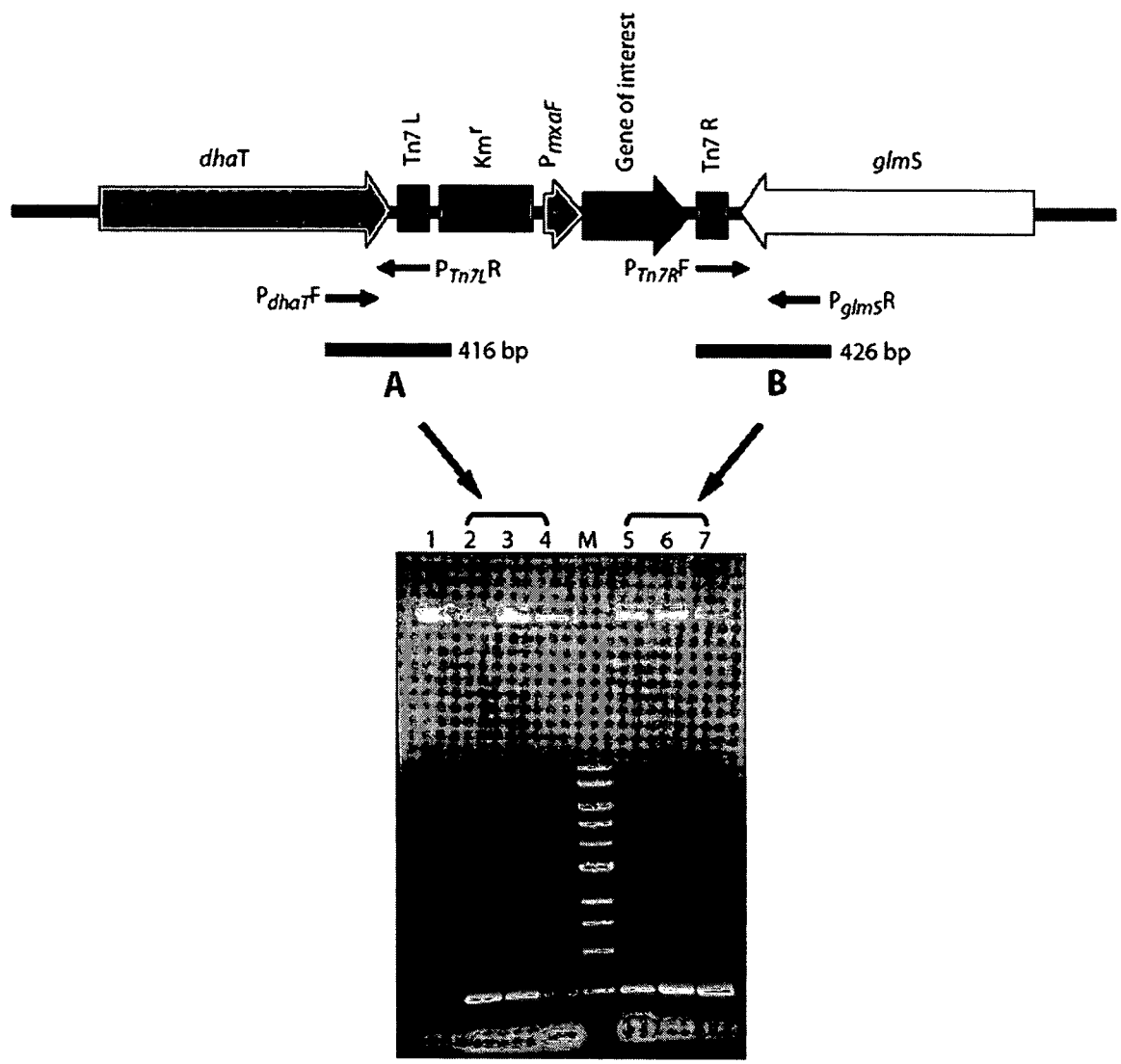

It has been recently shown that the Tn7 system integrates, in a stable manner, recombinant DNA fragments into a specific site of the chromosome called attTn7. This attTn7 is located in the intergenic region downstream of the glmS gene in many Gram negative bacteria such as *E. coli, Klebsiella pneumonia, Serratia marcescens, Pseudomonas putida* and *Yersinia pestis* (Craig, 1989; Lichtenstein and Brenner, 1982; Choi et al., 2005). Southern hybridization analysis of three recombinants confirmed that Tn7 integration occurred in the chromosomal DNA of *M. extorquens* (FIG. 2). Nucleotide sequence analyses cloned genes tested (bgl, estI and gfp) revealed the identity of the Tn7 integration site(s) in *M. extorquens*. Interestingly, all three genes were integrated at the same site of the chromosome. The Tn7 insertion site was located in a 61 bp intergenic region between glmS, which encodes the essential glucosamine-6-phosphate synthetase, and dhaT, which encodes 1,3-propanediol dehydrogenase in the chromosome of *M. extorquens*. Sequence analysis of cloned DNA fragments showed that Tn7 system was inserted between nucleotides 24 and 25 downstream of the glmS stop codon (FIG. 3), and this site seems to lie in one of the inverted repeats of the putative glmS transcriptional terminator, as had been previously suggested (Choi et al., 2005). To confirm the integration of target genes in the chromosome of *M. extorquens*, colony PCR was carried out by using two sets of Tn7 based primers and two sets of strain specific primers as described in material and methods. The PCR products resulting from different colonies were similar in size as expected, showing that the mini-Tn7 transposon had inserted in one orientation into one specific area of the *M. extorquens* chromosome downstream of glmS (FIG. 4).

Taken together, these results indicate that *M. extorquens* has a unique Tn7 attachment site (attTn7), and the insertion does not cause any insertional inactivation of host genes. This attTn7 is a useful site for the integration of recombinant genes in *M. extorquens* with the ultimate purpose of heterologous protein production.

Integrative expression of heterologous proteins in *M. extorquens*. The mini-Tn7 based recombinant plasmids were integrated into the attTn7 locus of *M. extorquens* by electroporation. Electroporation of the *M. extorquens* strain with these constructs in conjunction with the helper plasmid yielded about ~$10^3$ transformants on selective plates containing 50 µg/ml of kanamycin. The mini-Tn7 integrated expression cassettes containing either bgl, estI or gfp under the control of P, F promoter were successfully integrated and the respective genes were expressed in *M. extorquens*. The positive clones producing active recombinant proteins were screened on CHOI plates containing chromogenic substrates, X-gal for β-galactosidase, X-caprylate for esterase. Recombinant GFP was detected by fluorescence microscopy or by spectrofluorophotometry as mentioned in the materials and methods.

Figure 5:
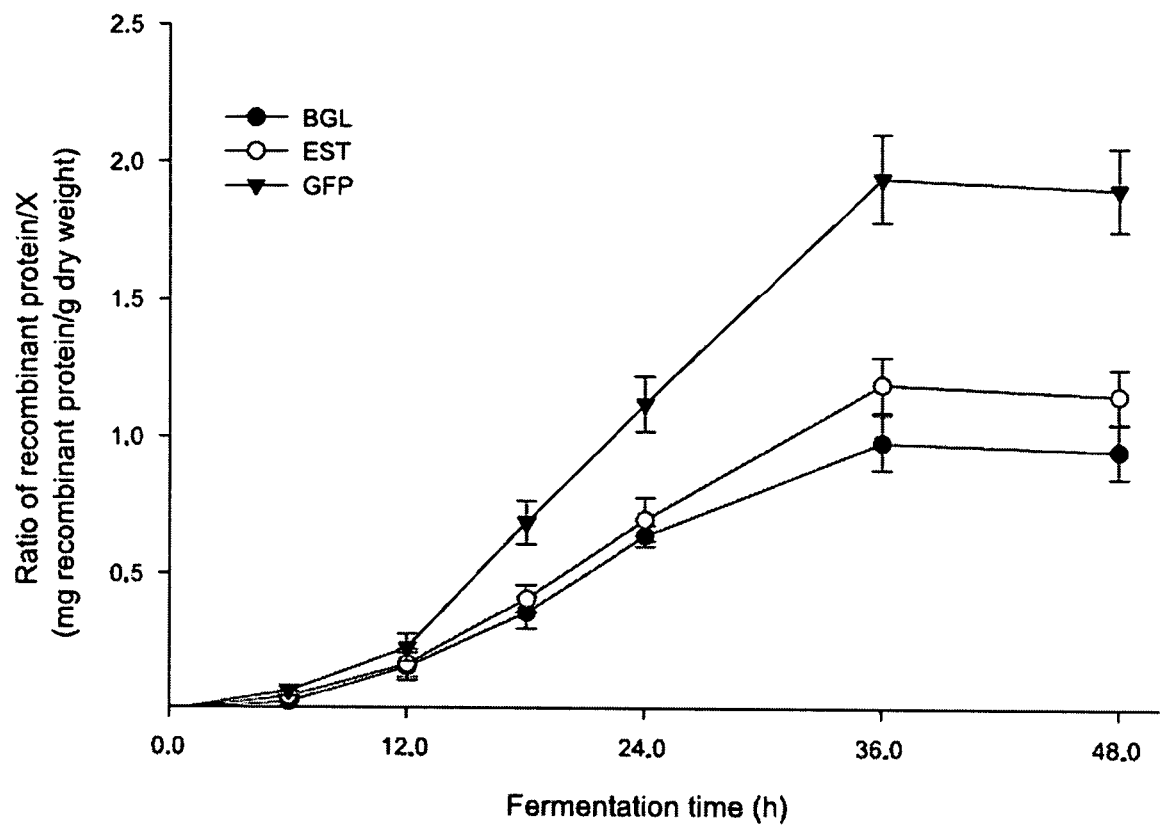
FIG. 5 is a graph comparing the yield of target protein from recombinant *M. extorquens* for one copy of gene integrated in the chromosome under the control of the $P_{mxaF}$.

High-cell-density fermentations were performed with strains BGL, EST, and GFP1. A previously developed fermentation protocol for *M. extorquens* was conducted (Bélanger et al., 2004). This strategy was proven to be very effective in achieving high biomass yields of *M. extorquens* ATCC 55366, using methanol as a carbon source and energy source (Bourque et al., 1995). In this study, the nitrogen source was not limiting, in order to reduce cellular poly-β-hydroxy butyric acid (PHB) production and accumulation. PHB production, a result of substrate limitation, was monitored by microscopy and by chemical means throughout the duration of the fed-batch fermentation. The PHB granules accumulated only at the end of the fermentation, approximately after 50-60 h run time, and never exceeded 20% of the biomass (data not shown). The growth of recombinant *M. extorquens* carrying either the bgl, estI or gfp genes showed that the maximum recombinant protein yield was reached at late exponential phase (0.9, 1.1 and 1.9 mg per g dry biomass, respectively), and subsequently decreased slightly as the culture reached early stationary phase (FIG. 5).

Figure 6:
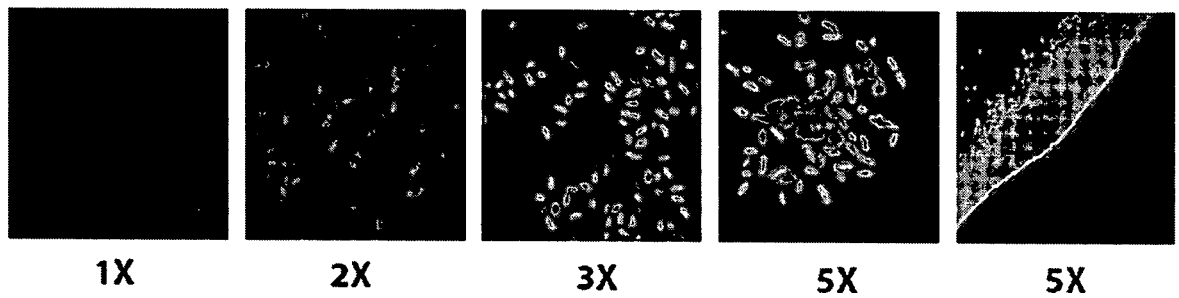
FIG. 6 is a series of drawings illustrating the integrative expression of multi-copy GFP in *M. extorquens*.
Figure 7:
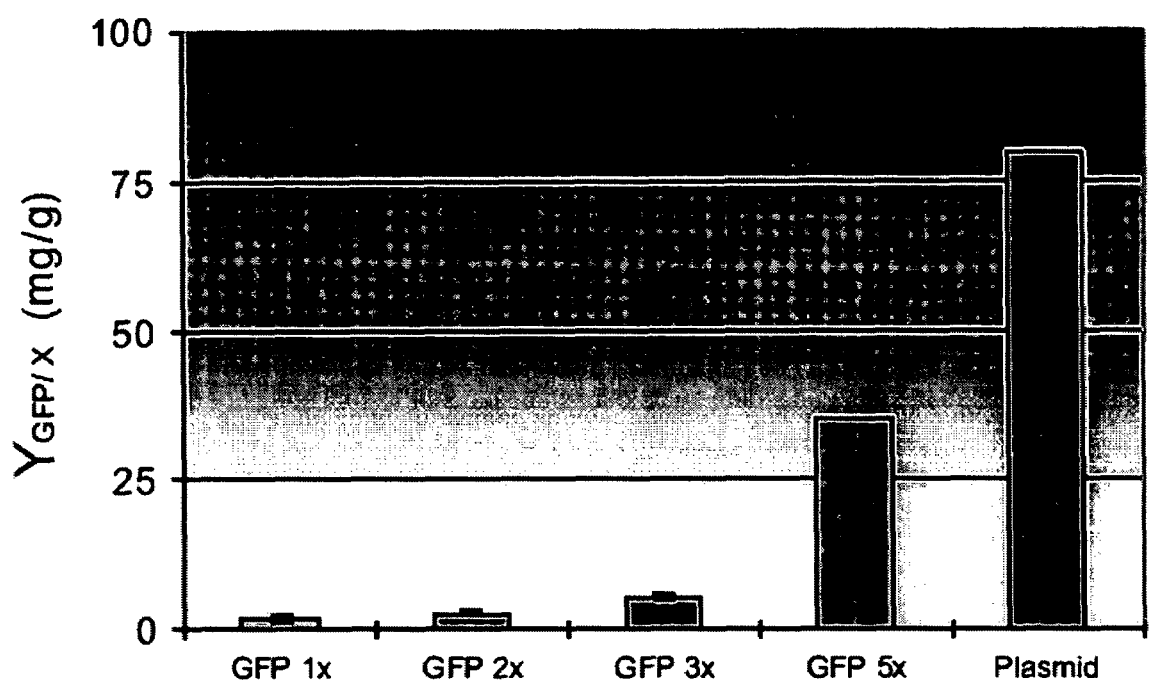
FIG. 7 is a graph comparing the specific yield of GFP from recombinant *M. extorquens* for various GFP gene copy numbers integrated in the chromosome and for GFP gene encoded in the plasmid DNA.

Multi-copy integration and expression of GFP. In yeasts, multi-copy gene integration methods have been applied for the purpose of increasing recombinant protein expression levels. However, this approach has not been commonly used in prokaryotes. Typically, during high cell density pilot scale production of recombinant proteins, segregational instability resulting in partial or complete loss of plasmids is a common occurrence. Furthermore, utilization of antibiotics for selection in bioprocesses can be a regulatory issue, as well as a major problem for downstream processing. However, cloned genes must be stably maintained in the culture in order to achieve robust and productive recombinant cell processes. Since integration of gene(s) into the chromosomes eliminates the segregational instability and copy number variation associated with plasmid-based systems, we constructed one-, two-, three-, and five-copy integrations of the gfp expression cassettes in the chromosome of *M. extorquens*, and protein expression levels were evaluated. Expression cassettes, GFP1, GFP2, GFP3, and GFP5, were made, each copy with the cassette containing the open reading frame of gfp under the control of the $P_{mxaF}$ promoter and a RBS as shown FIG. 1. The expression cassette was cloned into the integration vector pBR170, generating four separate integration vectors containing one, two, three and five copies of the gfp gene. A wild type culture (non-transformed competent cells) of *M. extorquens* was electroporated with these vectors and colonies were selected on a CHOI medium plate containing kanamycin. One colony from each copy number construct (GFP1, GFP2, GFP3 and GFP5) was selected and GFP activity was verified under the fluorescence microscopy (FIG. 6). Growth of recombinant cultures containing chromosomally integrated multi-copies of gfp genes (GFP1, GFP2, GFP3 and GFP5) resulted in the production of 1.9, 2.9, 5.5, and 35.1 mg GFP/g dry biomass, respectively (FIG. 7). In this experiment, the amount of biomass generated from these multi-copy integrants at the end of fermentation (~48 h) was essentially identical to the wild type strain (~40 g dry mass per liter, data not shown), which indicates that gene dosage does not negatively affect the fermentation capability of *M. extorquens*.

The results of the specific yields showed that the GFP production was enhanced as additional copies of the gfp gene were integrated in the chromosome. The specific yield was proportional to the number of integrated genes. However, when 5 copies of gfp were integrated, proportionality was lost. The specific yield of the five copy construct showed approximately a 20 fold higher yield (35.1 mg/g) than the levels produced by single copy integrants, and this reached almost 50% of the production yield obtained by the plasmid-based production system (FIG. 7). To evaluate the stability of multi-copy gfp integrated clones, GFP yields were determined once every 30 generations for a total of 120 generations in the absence of antibiotic selection. GFP production yields remained constant (data not shown).

Taken all together, we believe that the multi-copy integration system is be a useful and efficient tool for the purpose of stable recombinant protein production in the absence of selective pressure in *M. extorquens*.

Materials and Methods

Bacterial strains, plasmids and growth conditions. The bacterial strains and plasmids used in this study are listed in Table 1.

*E. coli* was cultured in Luria Bertani broth (LB) at 37° C. Strain of *M. extorquens* ATCC 55366 was grown in CHOI medium, as previously described (Bourque at al., 1995, Bélanger et al., 2004, the disclosures of which are incorporated herein by reference) and 1% (v/v) methanol was used as sole carbon source. Both media were solidified by 1.8% agar (Difco) when appropriate. Antibiotics were used for *E. coli* and *M. extorquens* at the following concentrations (in µg/ml): ampicillin, 100; kanamycin (Km), 40; tetracyclin (Tc), 35. The mini-Tn7 recombinant plasmids and the helper plasmid pUX-BF13, were purified from *E. coli*.

TABLE 1

Strains and plasmids used in this study

| Strain or plasmid | Description | Reference or source |
|---|---|---|
| *M. extorquens* strains | | |
| ATCC 55366 | Wild-type | ATCC |
| BGL | One copy integrant of the lactase cassette derived from pBRI-bgl | This study |

TABLE 1-continued

Strains and plasmids used in this study

| Strain or plasmid | Description | Reference or source |
| --- | --- | --- |
| EST | One copy integrant of the esterase cassette derived from pBRI-est | This study |
| GFP1 | One copy integrant of the gfp cassette derived from pBRI-gfp1 | This study |
| GFP2 | Two copies integrant of the gfp cassette derived from pBRI-gfp2 | This study |
| GFP3 | Three copies integrant of the gfp cassette derived from pBRI-gfp3 | This study |
| GFP5 | Five copies integrant of the gfp cassette derived from pBRI-gfp5 | This study |
| *E. coli* strains | | |
| Top10 | Strain for cloning and propagating plasmid DNA | Invitrogen Inc. |
| S-17/λ pir | Host strain for pUX-BF13 | Bao et al., 1991 |
| Plasmids | | |
| pCR2.1-TOPO | PCR cloning vector | Invitrogen Inc. |
| pCR-bgl | pCR2.1-TOPO plasmid containing lactase expression cassette | This study |
| pCR-est | pCR2.1-TOPO plasmid containing esterase expression cassette | This study |
| pCR-gfp1 | pCR2.1-TOPO plasmid containing one copy of gfp expression cassette | This study |
| pCR-gfp2 | pCR2.1-TOPO plasmid containing two copies of gfp expression cassette | This study |
| pUC19 | Multi-purpose cloning vector | Invitrogen Inc. |
| pCM-bgl | pCM110 plasmid containing lactase expression cassette | This study |
| pCM-est | pCM110 plasmid containing esterase expression cassette | This study |
| pCM-gfp | pCM110 plasmid containing gfp expression cassette | This study |
| pBK-miniTn7-ΩSm2 | pUC19-based delivery plasmid for a miniTn7-Km transposon; Km$^r$, Sm$^r$ | Koch et al., 2001 |
| pBRI70 | pUC19-based delivery plasmid for a miniTn7-Km transposon; Km$^r$ | This study |
| pBRI-bgl | pBRI70 plasmid containing lactase expression cassette | This study |
| pBRI-est | pBRI70 plasmid containing esterase expression cassette | This study |
| pBRI-gfp1 | pBRI70 plasmid containing one copy of gfp expression cassette | This study |
| pBRI-gfp2 | pBRI70 plasmid containing two copies of gfp expression cassette | This study |
| pBRI-gfp3 | pBRI70 plasmid containing three copies of gfp expression cassette | This study |
| pBRI-gfp5 | pBRI70 plasmid containing five copies of gfp expression cassette | This study |
| pUX-BF13 | R6K replicon based helper plasmid | Bao et al., 1991 |
| pCESTa | Esterase gene source | Choi et al., 2004 |
| pBGLIII | Lactase gene source | Hung et al., 2001 |
| pQBI63 | GFP gene source | Qbiogene Inc. |

DNA isolation and manipulations. Plasmids from *E. coli* were prepared with the Qiagen mini plasmid purification kit according to the manufacturer's instructions (Qiagen Inc., Mississauga, ON, Canada). Recombinant plasmids were constructed and agarose gel electrophoresis was performed according to the method of Sambrook and Russell (2000). DNA fragments were isolated from agarose gels by using QIAquick gel extraction system (Qiagen). T4 DNA ligase, and other DNA modifying enzymes were purchased from New England Biolabs Inc., GIBCO/BRL Life Technologies, Inc., or Pharmacia LKB Biotechnology and used as recommended by the manufacturer. Electroporation was performed with a Gene-Pulser II electroporation apparatus (Bio-Rad Laboratories, Mississauga, ON, Canada).

Construction of Tn7 vectors. The mini-Tn7 base vector pBR170 for *M. extorquens* was constructed as follows: the $P_{mxaF}$-ribosomal binding site (RBS) was amplified from pCESTc (Choi et al., 2004) using primers MDH-F-PstI (5'-GGCTGCAGGTTGACGACAACGGTGCGATG-3') (SEQ. ID NO.: 2) and MDH-R-MluI (5'-CCGACGCGTATG-TATATCTCCTTCTTAAAG-3') (SEQ. ID NO: 3). The PCR fragment containing $P_{mxaF}$-RBS was cloned into pBK-miniTn7-KmΩSm1 (Koch et al., 2001) which was partially digested with PstI/MluI to delete SmRISpR cassette, to generate pBRI70 (FIG. 1A).

The 2.1 kb fragment carrying the lactase gene (bgl) was amplified from pEGIG4 (Hung et al., 2001) using primers bgl-F-MluI (5'-CACGCGTATG GAACATAGAGCGT-TCAAGTG-3') (SEQ. ID NO: 4) and bgl-R-NotI (5'-GCG-GCCGCTTACAGCTTGACGACGAGTACGCCG-3') (SEQ ID NO: 5). For the amplification of esterase gene (1.8 kb, estI), pCESTa (Choi et al., 2004) was used as a template with primers est-F-MluI (5'-GACGCGTATGGAT- CAATCTAAAACAAATC-3') (SEQ ID NO: 6) and est-R-KpnI (5'-CGGTACCTTATTTATTTGTAATACCGTCTGC-3') (SEQ ID NO: 7).

The 0.8 kb fragment carrying the gfp gene was amplified with pCM110-gfp using primers gfp-F-MluI (5'-GACGCG-TATGGCTAGCAAAGGAGAAGAAC-3') (SEQ. ID NO: 8) and gfp-R-AflII (5'-CCTTAAGTCAGTTGTACAGT-TCATCCATGC-3') (SEQ. ID. NO. 9). All of PCR products were then cloned into pCR2.1-TOPO vector generating pCR-bgl, pCR-est, and pCR-gfp, respectively. The expression cassette was then cloned into the integration vector pBR170 to form pBR1-bgl, pBR1-est, and pBR1-gfp, respectively (FIG. 1B, C, D). Similarly, three recombinant plasmids pBR1-gfp2, pBR1-gfp3, and pBR1-gfp5, containing two, three and five copies of the gfp expression cassette, were constructed with different restriction enzyme sites available in the MCS of pBR170, respectively. (FIGS. 1E-G).

Chromosomal integration of constructs by electroporation. Competent *M. extorquens* cells (100 µl suspension) were mixed in an eppendorf tube with 0.5 µg of plasmid DNA (pBRI derivatives) and 0.5 µg of helper plasmid containing genes encoding the transposition proteins necessary for insertion of the Tn7 cassette into the genomic target site (Bao et al., 1991). The mixture was transferred to an ice-cold electroporation cuvette and treated in a Bio-Rad electroporator (25 pF, 200Ω, 5 ms, 2.5 kV/cm). Immediately thereafter, 1 ml of CHOI medium was added to the cuvette. The cell suspension was transferred to 15 ml tube and incubated at 30° C. for 5 h, then 100 µl of culture was spread on selective plates (CHOI agar with 35 µg of kanamycin per ml). The plates were incubated at 30° C. for 48 h until Km$^r$ colonies appeared. Typically, about 300-500 transformants per plate were obtained.

Southern blot analysis. Chromosomal DNA was purified from mini-Tn7-Km-target gene transformed *M. extorquens* by using AquaPure Genomic DNA kit (Bio-Rad) as recommended by the manufacturer. DNA samples (~2 µg) were digested with SalI separated electrophoretically on a 0.7% agarose gel, and transferred to a Hybond N membrane (Amersham Biotech. Inc.) according to the instructions of the supplier. The PCR fragment of each target genes (bgl, estI and gfp) were labeled separately with digoxigenin-11-dUTP (DIG) (Roche Applied Science) and used as a probe. After hybridization at 42° C. for 12 h and being washed twice in 2×SSC with 0.2% sodium dodecyl sulfate (SDS) at room temperature, the DIG-labeled fragments were detected by reaction with anti-DIG antibodies coupled to alkaline phosphatase, according to a protocol supplied by the manufacturer (Roche Applied Science). Nylon membranes were stained with substrate solution (NBT/BCIP) for 5 min.

Determination of Tn7 insertion site in *M. extorquens*. For the verification of Tn7 insertion site, we cloned the DNA flanking the Tn7 insertion site in recombinant *M. extorquens*. To subclone the Tn7 insertion site from recombinant *M. extorquens*, SalI digested chromosomal DNA was cloned into the unique SalI site of the pUC19 vector and transformed into *E. coli* TOP10. Since the $P_{mxaF}$ promoter is not recognized by *E. coli*, a kanamycin resistant clone was selected for sequencing. The sequencing was done by primer walking on purified plasmid DNA. The first primers recognized the vector sequences and both strands were sequenced. The nucleotide sequences of both strands were determined by AmpliTaq FS DNA polymerase fluorescent dye terminator reactions as recommended by the supplier (Perkin-Elmer). Sequencing products were detected by using an Applied Biosystems 373 stretch automated sequencer (Applied Biosystems). Nucleotide sequences were conducted on *M. extorquens* genome databases provided by Integrated Genomics and PEDANT; Protein Extraction, Description and ANalysis Tool.

The integration of target genes were also confirmed by colony PCR using primers ($P_{Tn7L}R$; 5'-ATTAGCTTACGACGCTACACCC-3' (SEQ ID NO: 10), $P_{Tn7R}F$; 5'-CACAGCATAACTGGACTGATTTC-3' (SEQ. ID NO. 11), $P_{dhaT}F$; 5'-CATCGCGATTGTCGATTCGG-3' (SEQ. ID NO. 12), and $P_{glmS}R$; 5'-CTGAAGGAAATCAGCTACATC-3' (SEQ. ID. NO. 13)) as shown in FIG. 4.

Gene expression and protein assays. Detection of GFP was carried out by fluorescence microscopy, and quantified by spectrofluorophotometry (Shimadzu RF-5001PC). The measurements were carried out with whole cells resuspended in phosphate-buffered saline (PBS). The excitation wavelength was 397 nm and the emission wavelength was 510 nm. The esterase activity was determined by a spectrophotometric method using para-nitrophenyl caprylate (pNP-caprylate) as substrate. The rate of hydrolysis of pNP-caprylate at 37° C. was measured in 50 mM sodium phosphate buffer (pH 7.0) according to Kademi et al. (1999). The β-galactosidase activity was measured with o-nitrophenyl-β-D-galactoside (ONPG) as a substrate and calculated based on pure enzyme from *E. coli* (Sambrook and Russell, 2001). Protein concentration was estimated by the method of Bradford (1976) using the Bio-Rad protein assay kit (Bio-Rad) with bovine serum albumin as a standard.

Fed-batch fermentation. Recombinant *M. extorquens* fed-batch cultures were performed using a 20-L continuously stirred baffled fermentor (Chemap, Volkestwill, Switzerland) equipped with pH and $pO_2$ probes (Ingold), a foam sensor, and a mechanical foam breaker. For agitation, the bioreactor was equipped with 3 Rushton impellers. The dissolved oxygen level was controlled at 15% saturation by first, increasing agitation speed from 500 rpm to 1,000 rpm and then, by increasing the airflow supply from 7-8 L/min with pure oxygen. This $O_2$ enrichment was initiated after 30 h fermentation time at a initial feed rate of 0.2 L/min of pure oxygen, and was later increased up to 3 L/min. At the same time, airflow was reduced to keep an overall inlet gas rate of 8 L/min. The pressure in the fermentor was also increased to up 0.8 bar around 25 h fermentation for increasing the oxygen mass transfer.

Fed-batch bioreactor experiments were conducted at pH 7.0 and 30° C. Ammonia solution (30%) was used as both pH control and nitrogen source, and was added as needed during fermentation. A 1% inoculum grown in 1 L shake flasks was used to inoculate a 20 L fermentor containing 9 L of medium CHOI medium.

On-line measurements of the methanol concentration in the culture medium was performed using a silicone membrane probe (Bioengineering Inc.) coupled with a semiconductor gas sensor (Bourque et al., 1995). The methanol concentration was controlled by using an the adaptive control algorithm described previously (Bélanger et al., 2004). Methanol was added using a variable-speed peristaltic pump and the methanol concentration was controlled at 1.4 g/l. Off-gas measurements were performed for $O_2$ (Servomex Paramagnetic analyzer) and $CO_2$ (Servomex Infrared analyzer) concentrations.

It is understood that the examples described above in no way serve to limit the true scope of this invention, but rather are presented for illustrative purposes.

REFERENCES

1. Amaratunga, K., Goodwin, P. M., O'Connor, D., and Anthony, C. 1997. The methanol oxidation genes mxaFJ-GIR(S)ACKLD in *Methylobacterium extorquens*. FEMS Microbiol. Lett., 146, 31-38.
2. Bao, Y., Lies, D., Fu, H., and Roberts, G. P. 1991. An improved Tn7 system for the single-copy insertion of cloned genes into chromosomes of Gram-negative bacteria. Gene 109:167-168
3. Beland, M., D. Bourque, M. Perrier, and Míguez, C. B. 2004. On-line estimation of stoichiometric growth parameters for *Methylotrophic extorquens*. 9th International Symposium on Computer Applications in Biotechnology, Nancy, France, March 2004.
4. Bélanger, L., Figueira, M. M., Bourque, D., Morel, L., Beland, M., Laramée, L., Groleau, D., and Míguez, C. B. 2004. Production of heterologous protein by *Methylobacterium extorquens* in high cell density fermentation. FEMS Microbiol. Lett., 231, 197-204.
5. Bourque, D., Ouellette, B., Andr̂e, G., and Groleau, D. 1992. Production of poly-3-hydroxybutyrate from methanol: characterization of a new isolate of *Methylobacterium extorquens*. Applied Microbiology and Biotechnology, 37, 7-12.
6. Bourque, D., Pomerleau, Y., and Groleau, D. 1995. High cell density production of poly-beta-hydroxybutyrate (PHB) from methanol by *Methylobacterium extorquens*: production of high-molecular-mass PHB. Appl. Microbiol. Biotechnol. 44, 367-376.
7. Bradford, M. M. 1976. A rapid and sensitive method for the quantitation of microgram quantities of protein utilizing the principle of protein-dye binding. Anal. Biochem. 72:248-254.
8. Choi, K. H., Gaynor, J. B., White, K. G., Lopez, C., Bosio, C. M., Karkhoff-Schweizer, R. R., and Schweizer, H. P.

2005. A Tn7-based broad-range bacterial cloning and expression system. Nat. Methods. 2(6):443-8.
9. Choi, Y. J., Míguez, C., and Lee, B. H. 2004. Characterization and heterologous gene expression of a novel esterase from *Lactobacillus casei* CL96. Appl. Environ. Microbiol. 70, 3213-3221.
10. Craig, N. 1989. Transposon Tn7. In: D. E. Berg and M. M. Howe, Edit., *Mobile DNA*, American Society for Microbiology, Washington, D.C. pp. 211-225.
11. Idris, R., Trifonova, R., Puschenreiter, M., Wenzel, W. W., and Sessitsch, A. 2004. Bacterial communities with flowering plants of the Ni Hyperaccumulator *Thlaspi goesingense*. Appl. Environ. Microbiol. 70:2667-2677.
12. Figueira, M. M., Laramée, L., Murrell, J. C., Groleau, D. and Míguez, C. B. 2000. Production of green fluorescent protein by the methylotrophic bacterium *Methylobacterium extorquens*. FEMS Microbiol. Lett. 193, 195-200.
13. Fitzgerald, K. A. and Lidstrom, M. E. 2003. Overexpression of a heterologous protein, haloalkane dehalogenase, in a poly-β-hydroxybutyrate-deficient strain of the facultative methylotroph *Methylobacterium extorquens* AM1. Biotechnol. Bioeng. 81, 263-268.
14. Gallego, V, Garcia, M. T., and Ventosa, A. 2005. *Methylobacterium hispanicum* sp. Nov. and *Methylobacterium aquaticum* sp. Nov., isolated from drinking water. International Journal of Systematic and Evolutionary Microbiology 55:281-287.
15. Gutierrez, J., Bourque, D., Choi, Y., Criado, R., Cintas, L. M., Hernandez, P. E., and Míguez, C. B. 2005. Heterologous extracellular production of enterocin P from *Enterococcus faecium* P13 in the methylotrophic bacterium *Methylobacterium extorquens*. FEMS Microbiol. Lett. 248:125-131.
16. Hojberg, O., Schnider, U., Winteler, H. V., Sorensen, J., and Haas, D. 1999. Oxygen-sensing reporter strain of *Pseudomonas fluorescens* for monitoring the distribution of low-oxygen habitats in soil. Appl. Environ. Microbiol. 65, 4085-4093.
17. Hung, M., Xia, Z., Hu, N., and Lee, B. 2001. Molecular and Biochemical Analysis of Two β-Gal from *Bifidobacterium infantis*. Appl. Environ. Microbiol. 67: 4256-4263.
18. Kademi, A., N. Ait-Abdelkader, L. Fakhreddine, and Baratti, J. C. 1999. Thermostable esterase activity from newly isolated moderate thermophilic bacterial strains. Enzyme Microb. Technol. 24:332-338.
19. Koch, B., Jensen, L. E., and Nybroe, O. 2001. A panel of Tn7-based vectors for insertion of the gfp marker gene or for delivery of cloned DNA into Gram-negative bacteria. J. Microbiol. Methods 45, 187-195.
20. Koopmann, V. and Kutschera, U. 2005. In-vitro regeneration of sunflower plants, effects of a *Methylobacterium* strain on organ development. Journal of Applied Botany and Food Quality 79:59-62.
21. Lacava, P. T., Araujo, W. L., Marcon, J., Maccheroni Jr., W., and Azevedo, J. L. 2004. Interaction between endophytic bacteria from citrus plants and the phytopathogenic bacteria *Xylella fastidiosa*, casual agent of citrus-variegated chlorosis. Letters in Applied Microbiology 38:55-59.
22. Lichtenstein and Brenner, S. 1982. Unique insertion site of Tn7 in the *E. coli* chromosome. Nature 297:601-603.
23. Marx, C. J. and Lidstrom, M. E. 2001. Development of improved versatile broad host-range vectors for use in methylotrophs and other Gram-negative bacteria. Microbiology, 147, 2065-2075.
24. Pirttila, A. M., Laukkanen, H., Pospiech, H., Myllyla, R., and Hohtola, A. 2000. Detection of intracellular bacteria in the buds of scotch pine (*Pinus sylvestris* L.) by in situ hybridization. Appl. Environ. Microbiol. 66, 3073-3077.
25. Rickard, A., Leach, S., Hall, L., Buswell, C., High, N., and Handley, P. 2002. Phylogenetic relationships and coaggregation ability of freshwater biofilm bacteria. Appl. Environ. Microbiol. 68:3644-3650.
26. Romanovskaya, V., Stolyar, S., Malashenko, Y., and Dodatko, T. 2001. The ways of plant colonization by *Methylobacterium* strains and properties of these bacteria. Microbiology, 70, 221-227.
27. Sambrook, J. and Russel, D. W. 2000. Molecular Cloning. (third ed.), Cold Spring Harbor Laboratory, Cold Spring Harbor, N.Y.
28. Sy, A., Giraud, E., Jourand, P., Garcia, N., Willems, A., deLajudie, P., Prin, Y., Neyra, M., Gillis, M., Boivin-Masson, C., and Dreyfus, B. 2001. Methylotrophic *Methylobacterium* bacteria nodulate and fix nitrogen in symbiosis with legumes. J. Bacteriol. 183:214-220.
29. Van Dien, S. and Lidstrom, M. 2002. Stoichiometric model for evaluating the metabolic capabilities of the facultative methylotroph *Methylobacterium extorquens* AM1, with application to reconstruction of C3 and C4 metabolism. Biotechnology and Bioengineering, 78, 296-312.

The invention claimed is:

1. A vector for the integration of at least one gene into the genetic material of a *Methylobacterium* host cell such that the gene may be expressed by the host cell, the vector comprising a promoter operably linked to said at least one gene, and a transposon system, wherein the promoter is selected from the group consisting of a methanol dehydrogenase promoter, a lac promoter, a T5 promoter, and a λ promoter.

2. The vector of claim 1 wherein the transposon system is a mini-Tn7 transposon system.

3. The vector of claim 1 wherein the host cell is a *Methylobacterium extorquens* cell.

4. The vector of claim 1 wherein the promoter is a methanol dehydrogenase promoter.

5. The vector of claim 1 comprising one, two, three, four or five copies of the at least one gene.

6. The vector of claim 3 wherein the *Methylobacterium extorquens* host cell is of the species designated as ATCC 55366.

7. The vector of claim 1 wherein the at least one gene encodes a toxic protein.

8. The vector of claim 7 wherein the toxic protein is cry1Aa.

9. The vector of claim 1 wherein the at least one gene encodes a marker protein.

10. The vector of claim 9 wherein the protein is selected from the group consisting of β-galactosidase, esterase, and green fluorescence.

11. A *Methylobacterium* host cell transformed with a vector for the integration of at least one gene into the genetic material of the host cell such that the gene may be expressed by the host cell, the vector comprising a promoter operably linked to said at least one gene, and a transposon system.

12. The host cell of claim 11 that is a *Methylobacterium extorquens* cell.

13. The host cell of claim 11 wherein integration of the vector does not cause any insertional inactivation of host genes.

14. The host cell of claim 11 wherein the vector is integrated at the attTn7 site.

15. A method for producing a polypeptide encoded by said at least one gene, comprising the step of culturing host cells as claimed in claim 13.

16. A method for using the host cell as claimed in claim 13 as a biopesticide, wherein the at least one gene encodes a pesticide protein, the method comprising the step of applying one or more of the host cells to growing plants.

17. A method for using the host cell as claimed in claim 13 for tracking the movement and growth of the host cell, wherein the at least one gene encodes a marker protein, the method comprising the step of tracking the marker protein.

18. The method of claim 16 wherein the transposon system is a mini-Tn7 transposon system.

19. The method of claim 16 wherein the promoter is a methanol dehydrogenase promoter.

20. The method of claim 17 wherein the transposon system is a mini-Tn7 transposon system.

21. The method of claim 17 wherein the promoter is a methanol dehydrogenase promoter.

* * * * *

SEQUENCE LISTING

<160> NUMBER OF SEQ ID NOS: 13

<210> SEQ ID NO 1
<211> LENGTH: 61
<212> TYPE: DNA
<213> ORGANISM: Methylobacterium extorquens

<400> SEQUENCE: 1
gcggcgggag taccgctcgg cgcaccgatc cggccttcgg atcgatgcgc ctgccaacga    60
a                                                                  61

<210> SEQ ID NO 2
<211> LENGTH: 29
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 2
ggctgcaggt tgacgacaac ggtgcgatg                                              29

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccgacgcgta tgtatatctc cttcttaaag                                             30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacgcgtatg gaacatagag cgttcaagtg                                             30

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcggccgctt acagcttgac gacgagtacg ccg                                         33

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacgcgtatg gatcaatcta aaacaaatc                                              29

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cggtacctta tttatttgta ataccgtctg c                                           31

<210> SEQ ID NO 8
<211> LENGTH: 29
<212> TYPE: DNA
<213> ORGANISM: Artificial Sequence
```

```
-continued

<220> FEATURE:
<223> OTHER INFORMATION: Description of Artificial Sequence: Synthetic
      primer

<400> SEQUENCE: 8
gacgcgtatg gctagcaaag gagaagaac                                          29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccttaagtca gttgtacagt tcatccatgc                                         30

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attagcttac gacgctacac cc                                                 22

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cacagcataa ctggactgat ttc                                                23

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
catcgcgatt gtcgattcgg                                                    20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ctgaaggaaa tcagctacat c                                                  21
```